US008652110B2

(12) United States Patent
Yamamoto et al.

(10) Patent No.: US 8,652,110 B2
(45) Date of Patent: Feb. 18, 2014

(54) VALVE-EQUIPPED HAND SWITCH AND CHEMICAL LIQUID INTRODUCTION SYSTEM

(75) Inventors: Tetsuya Yamamoto, Osaka (JP); Michihiko Matsushima, Osaka (JP)

(73) Assignee: Sugan Co., Ltd., Osaka-Shi, Osaka (JP)

( * ) Notice: Subject to any disclaimer, the term of this patent is extended or adjusted under 35 U.S.C. 154(b) by 0 days.

(21) Appl. No.: 13/812,477

(22) PCT Filed: Jul. 26, 2010

(86) PCT No.: PCT/JP2010/062494
§ 371 (c)(1),
(2), (4) Date: Apr. 5, 2013

(87) PCT Pub. No.: WO2012/014267
PCT Pub. Date: Feb. 2, 2012

(65) Prior Publication Data
US 2013/0184576 A1  Jul. 18, 2013

(51) Int. Cl.
*A61M 5/00* (2006.01)
(52) U.S. Cl.
USPC .......................................... 604/246; 604/247
(58) Field of Classification Search
USPC .......... 604/19, 21, 30, 27, 244–256; 137/460, 137/461
See application file for complete search history.

(56) References Cited

U.S. PATENT DOCUMENTS

| | | | |
|---|---|---|---|
| 4,243,031 A * | 1/1981 | Genese | 604/118 |
| 6,866,654 B2 * | 3/2005 | Callan et al. | 604/247 |
| 2005/0234428 A1 * | 10/2005 | Spohn et al. | 604/533 |
| 2006/0213756 A1 * | 9/2006 | Takachi | 200/302.2 |
| 2010/0069748 A1 | 3/2010 | Yamamoto | |
| 2010/0191106 A1 | 7/2010 | Koyama | |
| 2013/0184576 A1 * | 7/2013 | Yamamoto et al. | 600/432 |

FOREIGN PATENT DOCUMENTS

| | | |
|---|---|---|
| JP | 2008-521577 A | 6/2008 |
| WO | 2004086438 A1 | 10/2004 |
| WO | 2006060688 | 6/2006 |
| WO | 2008081540 A1 | 7/2008 |
| WO | 2008155938 A | 12/2008 |

OTHER PUBLICATIONS

International Search Report issued in International Application No. PCT/JP2010/062494, dated Aug. 10, 2010.

* cited by examiner

*Primary Examiner* — Nicholas Lucchesi
*Assistant Examiner* — Niyati D Shah
(74) *Attorney, Agent, or Firm* — McDermott Will & Emery LLP

(57) ABSTRACT

In a valve-equipped hand switch and a chemical liquid introduction system, a contrast medium in a syringe is delivered to a patient line through a first port, a main passage around a spacer portion, and a second port. Furthermore, a pressure (about 300 psi) of the contrast medium delivered by a chemical liquid introduction device is transmitted as a reaction force through a third plunger from a handle portion of an operation piston held by an operator. As such, the operator can directly feel the pressure of the introduced contrast medium, which gives a sense of ease to the operator during operation.

7 Claims, 14 Drawing Sheets

VALVE-EQUIPPED HAND SWITCH AND CHEMICAL LIQUID INTRODUCTION SYSTEM

RELATED APPLICATIONS

This application is the U.S. National Phase under 35 U.S.C. §371 of International Application No. PCT/JP2010/062494, filed on Jul. 26, 2010, the disclosure of which Application is incorporated by reference herein.

TECHNICAL FIELD

The present invention relates to a valve-equipped hand switch and a chemical liquid introduction system used for controlling introduction of a chemical liquid by a chemical liquid introduction device for introducing the chemical liquid into a patient.

BACKGROUND ART

A cardiac catheter examination is conducted using a chemical liquid introduction device, with an affected area being contrasted. In coronary artery contrast for contrasting a cardiac blood vessel, an intravascular operation of dilating a stenosed lesion by catheterization is performed, for example. In left ventricle contrast for contrasting a left ventricle of a heart, movement of cardiac muscle around the left ventricle is examined based on a pattern of contraction and dilatation of the heart.

In controlling introduction of a contrast medium by a chemical liquid introduction device, a hand switch extending from the chemical liquid introduction device to the hand of an operator is used in order to perform contrast medium introduction control (flow rate control, volume control). Such hand switch is disclosed in International Patent Publication No. WO 2004-086438 (PTL 1) and International Patent Publication No. WO 2008-081540 (PTL 2).

With each of these hand switches, however, introduction of a contrast medium is controlled in accordance with information based on an amount of movement of a switch provided on the hand switch. Thus, the only feeling that is transmitted to the hand of the operator is a reaction from a spring member provided for returning the moving member in the hand switch to its initial position. The strength of reaction transmitted to the hand of the operator from this reaction is different from the actual pressure of an introduced contrast medium, which gives the operator a sense of unease.

CITATION LIST

Patent Literature

PTL 1: International Patent Publication No. WO 2004-086438
PTL 2: International Patent Publication No. WO 2008-081540

SUMMARY OF INVENTION

Technical Problem

A problem to be solved by the present invention is that the strength of reaction transmitted from a hand switch to a hand during operation of the hand switch is different from the actual pressure of an introduced contrast medium, which gives an operator a sense of unease. Therefore, the present invention was made to solve this problem, and an object of the present invention is to provide a valve-equipped hand switch, with which the strength of force transmitted from the hand switch to a hand during operation of the hand switch is felt equally to the actual pressure of an introduced contrast medium.

Solution to Problem

A valve-equipped hand switch based on the present invention includes a valve having a main passage with one open end side and the other closed end side, a first port in communication with a side portion of a central area of the main passage, a second port in communication with the side portion of the main passage closer to the other end side than the first port of the central area, a third port in communication with the side portion of the main passage closer to the other end side than the second port, and a fourth port in communication with the side portion of the main passage closer to the other end side than the second port, and also in communication with the second port.

The valve-equipped hand switch includes a first plunger fixedly arranged on the other end side in the main passage, for controlling a communicated state and a cutoff state between the third port and the fourth port, a second plunger slidably arranged in a liquid-tight manner in the main passage to divide the main passage into two segments, the one end side and the other end side, and also arranged with an elastic member interposed between itself and the first plunger, a third plunger slidably arranged in a liquid-tight manner in the main passage, on a tip end portion of an operation piston inserted into the main passage through the one end side, a spacer portion having a diameter smaller than an inner diameter of the main passage, and fixed to a side of the third plunger closer to the second plunger, and a detection device provided to operate in conjunction with movement of the operation piston, for detecting a rate of insertion and an amount of insertion movement of the operation piston in the main passage.

In an initial state, a communicated state between the third port and the fourth port is selected with the first plunger, and a cutoff state between the first port and the second port is selected with the second plunger.

In an operation state, a communicated state between the first port and the second port is selected by pushing the operation piston toward the other end side of the main passage, causing the spacer portion to oppose an elastic force resulting from compression of the elastic member while abutting the second plunger, to move the second plunger toward the other end side of the main passage, leading the spacer portion to be positioned between the first port and the second port, and a cutoff state between the third port and the fourth port is selected with the first plunger due to the first plunger being pushed by the elastic member.

In another embodiment, the first plunger includes an elastic member, and a circumferential surface of the first plunger bulges outward by being pushed by the elastic member, to attain a cutoff state between the third port and the fourth port.

In another embodiment, in a state where a pressure equal to or high than a prescribed pressure is applied from the first port, the second plunger is biased toward the other end side of the main passage by the pressure, to attain a cutoff state between the third port and the fourth port, and the third plunger and the spacer portion are biased toward the one end side of the main passage, to attain a communicated state between the first port and the second port.

In another embodiment, the first port is coupled to a chemical liquid line, the second port is coupled to a patient line, and the third port is coupled to a blood pressure monitor line. The chemical liquid line is coupled to an injector.

A chemical liquid introduction system based on the present invention includes a chemical liquid line coupled to an injector, a patient line, a blood pressure monitor line, and a valve-equipped hand switch including a first port coupled to the chemical liquid line, a second port coupled to the patient line, and a third port coupled to the blood pressure monitor line.

The valve-equipped hand switch includes a valve having a main passage with one open end side and the other closed end side, the first port is in communication with a side portion of a central area of the main passage, the second port is in communication with the side portion of the main passage closer to the other end side than the first port of the central area, the third port is in communication with the side portion of the main passage closer to the other end side than the second port, and the fourth port is in communication with the side portion of the main passage closer to the other end side than the second port, and also in communication with the second port.

The main passage includes therein a first plunger fixedly arranged on the other end side in the main passage, for controlling a communicated state and a cutoff state between the third port and the fourth port, a second plunger slidably arranged in a liquid-tight manner in the main passage to divide the main passage into two segments, the one end side and the other end side, and also arranged with an elastic member interposed between itself and the first plunger, a third plunger slidably arranged in a liquid-tight manner in the main passage, on a tip end portion of an operation piston inserted into the main passage through the one end side, a spacer portion having a diameter smaller than an inner diameter of the main passage, and fixed to a side of the third plunger closer to the second plunger, and a detection device provided to operate in conjunction with movement of the operation piston, for detecting a rate of insertion and an amount of insertion movement of the operation piston in the main passage.

In an initial state, a communicated state between the third port and the fourth port is selected with the first plunger, and a cutoff state between the first port and the second port is selected with the second plunger.

In an operation state, a communicated state between the first port and the second port is selected by pushing the operation piston toward the other end side of the main passage, causing the spacer portion to oppose an elastic force resulting from compression of the elastic member while abutting the second plunger, to move the second plunger toward the other end side of the main passage, leading the spacer portion to be positioned between the first port and the second port.

A cutoff state between the third port and the fourth port is selected with the first plunger due to the first plunger being pushed by the elastic member.

In a state where a pressure equal to or high than a prescribed pressure is applied from the first port coupled to the chemical liquid line, the second plunger is biased toward the other end side of the main passage by the pressure, to attain a cutoff state between the third port and the fourth port, and the third plunger and the spacer portion are biased toward the one end side of the main passage, to attain a communicated state between the first port and the second port.

In another embodiment, the chemical liquid line includes a segment of the chemical liquid introduction device and a segment of the valve-equipped hand switch that are attachable to/detachable from each other.

Advantageous Effects of Invention

According to the valve-equipped hand switch and the chemical liquid introduction system based on the present invention, a valve-equipped hand switch and a chemical liquid introduction system can be provided, with which the strength of force transmitted from the hand switch to a hand during operation of the hand switch is felt equally to the actual pressure of an introduced contrast medium.

DESCRIPTION OF EMBODIMENTS

A valve-equipped hand switch and a chemical liquid introduction system including this valve-equipped hand switch based on the present invention will be described. While the valve-equipped hand switch based on the present invention is applied to a contrast medium introduction system in medical practice as an application example of the present invention in an embodiment described below, the hand switch may be used for a chemical liquid introduction system that requires another similar system in medical practice.

In the embodiment described below, the same reference signs are used to identify the same or corresponding parts, and descriptions thereof may not be repeated. In addition, whenever any reference is made to a number, an amount and the like, the scope of the present invention is not necessarily limited to that number, amount and the like unless otherwise specified.

(Contrast Medium Introduction System)

Figure 1:
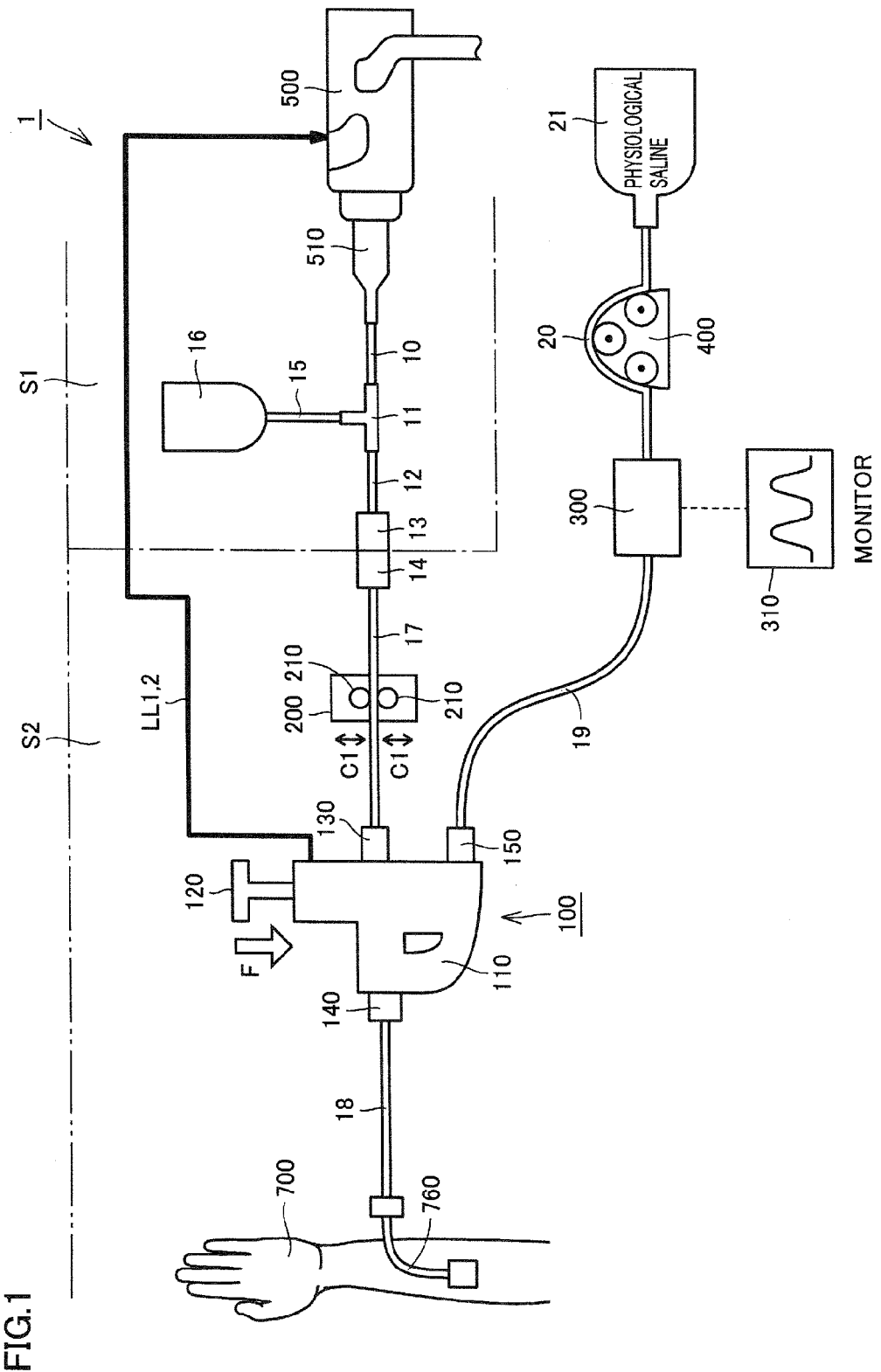
FIG. 1 is a schematic diagram showing the general structure of a chemical liquid introduction system in an embodiment.

Referring first to FIG. 1, a contrast medium introduction system including a valve-equipped hand switch 100 in this embodiment is described. FIG. 1 is a general schematic diagram showing a contrast medium introduction system 1 including valve-equipped hand switch 100 in this embodiment.

Valve-equipped hand switch 100 in this embodiment includes a valve 110 having a main passage therein, and valve 110 includes a first port 131, a second port 141, and a third port 151. A detailed structure of valve-equipped hand switch 100 will be described later.

First port 131 is coupled to one end of a chemical liquid line 17. A flow path opening/closing device 200 is provided in an intermediate area of chemical liquid line 17. Flow path opening/closing device 200 controls opening/closing of a flow path in chemical liquid line 17 by controlling a pair of movable objects 210 arranged to sandwich chemical liquid line 17 therebetween to move in a direction of an arrow C1 in the figure.

Chemical liquid line 17 has the other end coupled to one end of a flow path 12 via coupling connectors 13 and 14. Chemical liquid line 17 and flow path 12 are attachable to/detachable from each other via coupling connectors 13 and 14.

Flow path 12 has the other end coupled to a branch tube 11. Branch tube 11 is coupled to one end of a flow path 15 and one end of a flow path 10. Flow path 15 has the other end coupled to a contrast medium bag 16. Flow path 10 has the other end coupled to a syringe 510 containing a contrast medium. Syringe 510 is attached to a chemical liquid introduction device 500.

Second port 141 is coupled to one end of a patient line 18. Patient line 18 has the other end coupled to a catheter 760 attached to a patient 700.

Third port 151 is coupled to one end of a blood pressure monitor line 19. Blood pressure monitor line 19 has the other end coupled to a blood pressure measurement device (BPT) 300. Blood pressure measurement device (BPT) 300 is coupled to one end of a flow path 20. Flow path 20 has the other end coupled to a physiological saline bag 21. A roller pump 400 is provided in an area in some portion of flow path 20.

Before a cardiac catheter examination using a contrast medium is conducted, in valve-equipped hand switch 100, patient line 18 is coupled to blood pressure monitor line 19, and a blood pressure state of patient 700 is monitored by a monitor 310.

While a cardiac catheter examination using a contrast medium is conducted, the contrast medium in syringe 510 is introduced into patient 700 through flow path 10, flow path 12, chemical liquid line 17 and patient line 18, based on operation of chemical liquid introduction device 500 by an operator using an operation piston 120 of valve-equipped hand switch 100, or automatic operation of chemical liquid introduction device 500 by a computer.

(Valve-Equipped Hand Switch 100)

Figure 2:
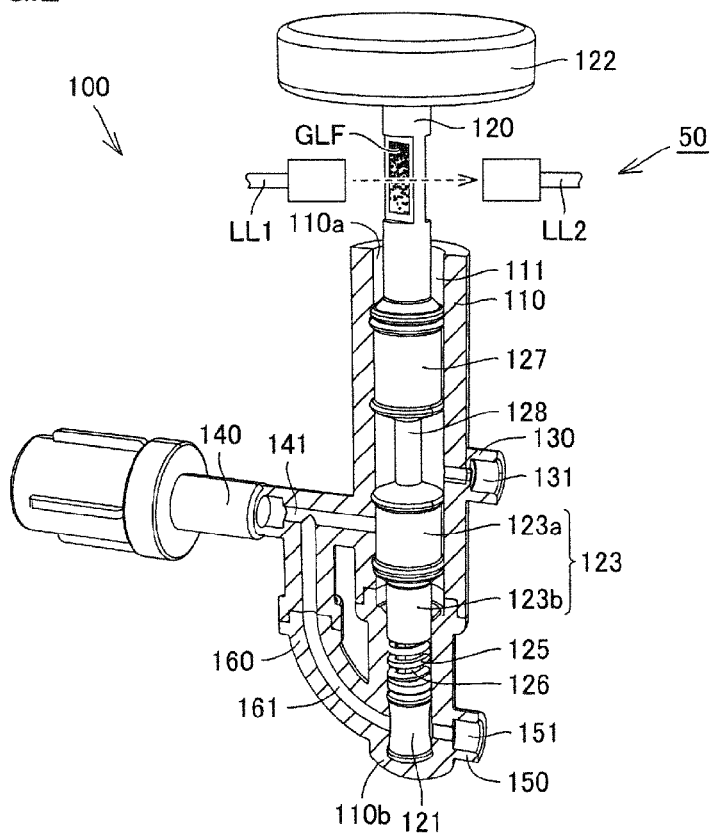
FIG. 2 is a vertical sectional view showing the structure of a valve-equipped hand switch in the embodiment.
Figure 3:
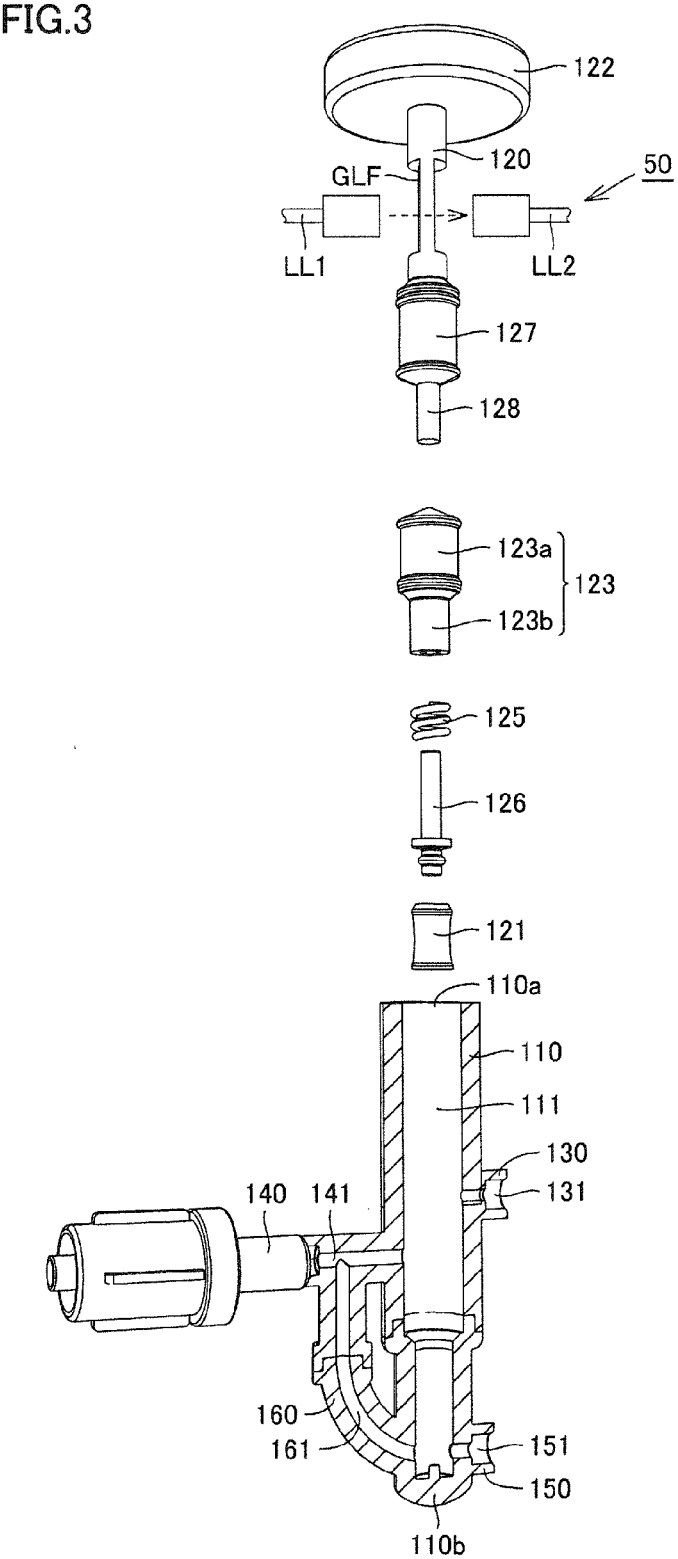
FIG. 3 is an exploded perspective view showing the structure of the valve-equipped hand switch in the embodiment.

Referring next to FIGS. 2 and 3, a detailed structure of valve-equipped hand switch 100 in this embodiment is described. FIG. 2 is a vertical sectional view showing the structure of valve-equipped hand switch 100, and FIG. 3 is an exploded perspective view showing the structure of valve-equipped hand switch 100. Valve-equipped hand switch 100 includes valve 110, as described above.

Valve 110 has a main passage 111 with one open end side 110a and the other closed end side 110b formed therein. A first branch tube 130 having first port 131 in communication with main passage 111 is provided on a side portion of a central area of main passage 111.

A second branch tube 140 having second port 141 in communication with main passage 111 is provided on the side portion of main passage 111 closer to other end side 110b than first port 131 of the central area. A third branch tube 150 having third port 151 in communication with main passage 111 is provided on the side portion of main passage 111 closer to other end side 110b than second port 141.

A coupling tube 160 having a fourth port 161 in communication with main passage 111 and also in communication with second port 141 is provided on the side portion of main passage 111 on the other end side opposite to third port 151.

A first plunger 121 for controlling a communicated state and a cutoff state between third port 151 and fourth port 161 is fixedly arranged on other end side 110b in main passage 111. First plunger 121 includes an elastic member such as rubber and elastomer.

First plunger 121 has a substantially cylindrical shape, and a concave surface having an outer circumference which is entirely concaved inward. The circumferential surface bulges outward by being axially pushed.

A second plunger 123 is slidably arranged in a liquid-tight manner in main passage 111 to divide main passage 111 into two sections, one end side 110a and other end side 110b, and also arranged with an elastic member 125 interposed between itself and first plunger 121. While elastic member 125 is formed of a coil spring, it is not limited to a coil spring.

Second plunger 123 includes a main plunger 123a located on one end side 110a of main passage 111, and an auxiliary plunger 123b located on other end side 110b of main passage 111. A spacer shaft 126 is provided between auxiliary plunger 123b and first plunger 121, and is inserted in internal space of elastic member 125. Second plunger 123 has space S therein in which spacer shaft 126 is slidably inserted (see FIG. 4).

Operation piston 120 is inserted through one end side 110a of main passage 111. A third plunger 127 slidably arranged in a liquid-tight manner in main passage 111 is provided on a tip end portion of operation piston 120. In addition, a spacer portion 128 having a diameter smaller than an inner diameter of main passage 111 is fixed to a side of third plunger 127 closer to second plunger 123. An opening of one end side 110a of main passage 111 is closed with a cap 124.

Operation piston 120 is provided with a handle portion 122. Operation piston 120 is further provided with a detection device 50 for detecting a rate of insertion and an amount of insertion movement of operation piston 120 in main passage 111.

In this embodiment, detection device 50 includes a gradation light transmission portion GLF formed in operation piston 120, a laser light application line LL1 for applying laser light to gradation light transmission portion GLF, and a laser light reception line LL2 for receiving the laser light transmitted through gradation light transmission portion GLF. Light information obtained from detection device 50 is input to chemical liquid introduction device 500 as a control signal of chemical liquid introduction device 500.

Detection device 50 is not limited to this structure. A known detection device capable of detecting an amount of movement and a speed of movement of operation piston 120 can be used.

(Operation of Valve-Equipped Hand Switch)

Figure 4:
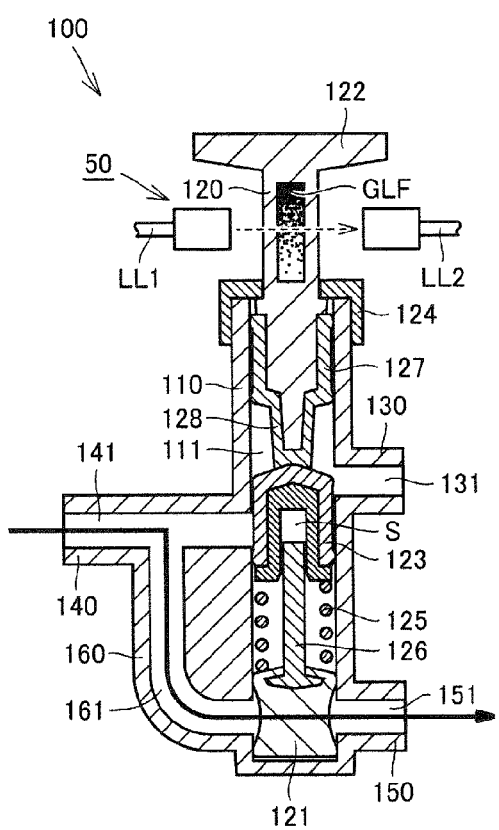
FIG. 4 is a schematic diagram showing an initial state of the valve-equipped hand switch in the embodiment.
Figure 5:
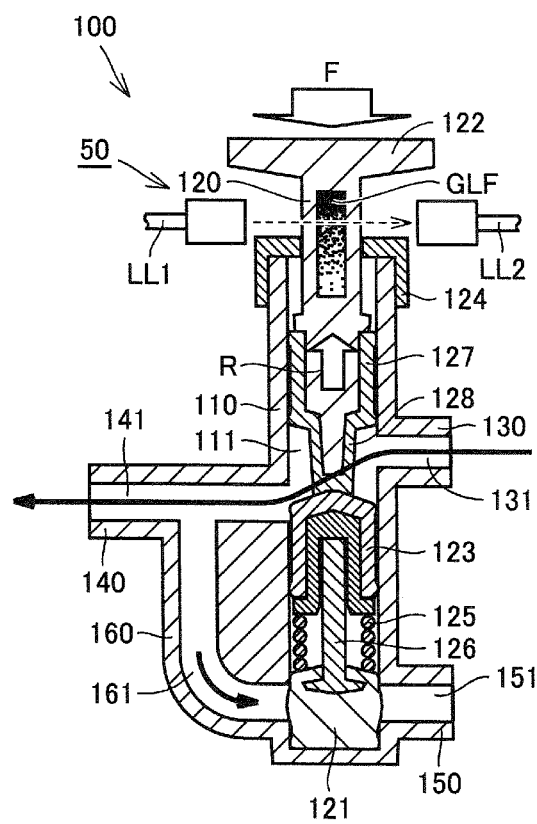
FIG. 5 is a schematic diagram showing an operation state of the valve-equipped hand switch in the embodiment.
Figure 6:
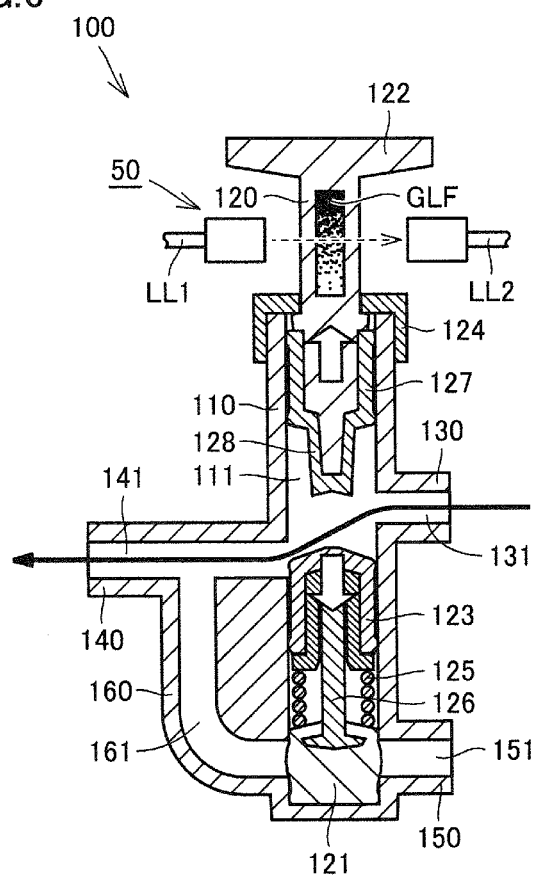
FIG. 6 is a schematic diagram showing a high-pressure state of the valve-equipped hand switch in the embodiment.

Referring now to FIGS. 4 to 6, operation of valve-equipped hand switch 100 in contrast medium introduction system 1 is described. FIG. 4 is a schematic diagram showing an initial state of valve-equipped hand switch 100, FIG. 5 is a schematic diagram showing an operation state of valve-equipped hand switch 100, and FIG. 6 is a schematic diagram showing a high-pressure state of valve-equipped hand switch 100.

(Initial State)

Referring to FIG. 4, an initial state of valve-equipped hand switch 100 is described. In the initial state of valve-equipped hand switch 100, a biasing force is not applied to elastic member 125, so that third port 151 and fourth port 161 are in communication with each other through a clearance formed between the circumferential surface of first plunger 121 and main passage 111. In addition, main plunger 123*a* of second plunger 123 is located in a position to close second port 141, so that first port 131 and second port 141 are cut off from each other.

As such, this initial state is a state before a cardiac catheter examination using a contrast medium is conducted. In valve-equipped hand switch 100, second port 141, fourth port 161 and third port 151 are in communication with one another, and patient line 18 is coupled to blood pressure monitor line 19, so that a blood pressure state of patient 700 is monitored by monitor 310.

(Operation State)

Referring to FIG. 5, an operation state where the operator pushes operation piston 120 is described. Generally, this operation state corresponds to an operation state of coronary artery contrast for contrasting a cardiac blood vessel. For example, a speed of a single introduction of the contrast medium by chemical liquid introduction device 500 is about 3 cc/sec, and an amount of introduction is about 6 cc.

When the operator pushes operation piston 120, light information obtained from detection device 50 is input to chemical liquid introduction device 500 as a control signal of chemical liquid introduction device 500. Based on this input information, the contrast medium in syringe 510 is delivered to first port 131.

Furthermore, by pushing operation piston 120 toward other end side 110*b* of main passage 111 (direction of an arrow F in the figure), spacer portion 128 opposes an elastic force resulting from compression of elastic member 125 while abutting second plunger 123, to move second plunger 123 toward other end side 110*b* of main passage 111.

Consequently, in valve-equipped hand switch 100, spacer portion 128 is positioned between first port 131 and second port 141, to bring first port 131 and second port 141 into communication with each other. In addition, since first plunger 121 is pushed by elastic member 125, a barrel portion of first plunger 121 serving as its circumferential surface bulges radially, to cut off third port 151 and fourth port 161 from each other.

As a result, the contrast medium in syringe 510 is delivered to patient line 18 through first port 131, main passage 111 around spacer portion 128, and second port 141. Furthermore, a pressure (about 300 psi) of the contrast medium delivered by chemical liquid introduction device 500 is transmitted as a reaction force R through third plunger 127 from handle portion 122 of operation piston 120 held by the operator. As such, the operator can directly feel the pressure of the introduced contrast medium, which gives a sense of ease to the operator during operation.

(High-Pressure State)

Referring to FIG. 6, a high-pressure state in valve-equipped hand switch 100 is described. Generally, this operation state corresponds to an operation state of left ventricle contrast for contrasting a left ventricle of a heart. For example, a speed of a single introduction of the contrast medium by chemical liquid introduction device 500 is from about 8 cc/sec to about 15 cc/sec, and an introduction amount is from about 15 cc to about 20 cc. An introduction pressure of the contrast medium by chemical liquid introduction device 500 is from about 800 psi to about 900 psi.

When the contrast medium in a high pressure state described above is introduced into first port 131 of valve-equipped hand switch 100, spacer portion 128 and third plunger 127 are biased toward one end side 110*a* of main passage 111 by the pressure. Second plunger 123 also moves toward other end side 110*b* of main passage 111 by the contrast medium in a high pressure state.

Consequently, first port 131 and second port 141 are in communication with each other. In addition, since first plunger 121 is pushed by elastic member 125, the barrel portion of first plunger 121 serving as its circumferential surface bulges radially, to cut off third port 151 and fourth port 161 from each other.

As a result, the contrast medium in syringe 510 is delivered to patient line 18 through first port 131, main passage 111 around spacer portion 128, and second port 141. Spacer portion 128 and third plunger 127 cannot be pushed back by the operator's force. As such, the operator can feel that the contrast medium in a high pressure state is being introduced, through handle portion 122 of operation piston 120.

According to valve-equipped hand switch 100 and contrast medium introduction system 1 including valve-equipped hand switch 100 in this embodiment as described above, when first port 131 through which the contrast medium is introduced becomes in communication with second port 141 in main passage 111, the pressure of the contrast medium can be provided to third plunger 127 that can be operated by the operator. As a result, the strength of force transmitted from the hand switch to a hand during operation of the hand switch by the operator is felt equally to the actual pressure of the introduced contrast medium, which gives a sense of ease to the operator during operation.

In addition, as shown in FIG. 1, valve-equipped hand switch 100 and contrast medium introduction system 1 including valve-equipped hand switch 100 in this embodiment include coupling connectors 13 and 14 between valve-equipped hand switch 100 and syringe 510. Thus, while operation of introducing the contrast medium into syringe 510 is performed by closing chemical liquid line 17 with flow path opening/closing device 200, a blood pressure state of patient 700 can be monitored by monitor 310 through blood pressure monitor line 19.

Furthermore, by providing coupling connectors 13 and 14 between valve-equipped hand switch 100 and syringe 510, the system can be separated into a segment S1 on the side of chemical liquid introduction device 500 and a segment S2 on the side of valve-equipped hand switch 100. Thus, segment S2 can be used once for each of several patients, and segment S1 can be used multiple times.

It is noted that FIGS. 1 to 3 show the general structure of valve-equipped hand switch 100 in order to explicitly indicate its functions. A valve-equipped hand switch 100A in an actually used state has an outer shape that can be held and operated readily by an operator 1000, as shown in FIGS. 7 and 8.

A grip body 170 made of resin incorporates therein valve-equipped hand switch 100 having the structure shown in FIGS. 2 and 3. A lever 120A coupled to operation piston 120 is provided on an upper surface of grip body 170, with a rear end portion of lever 120A and a rear end portion of grip body 170 being coupled to each other pivotally via a hinge H1.

Figure 7:
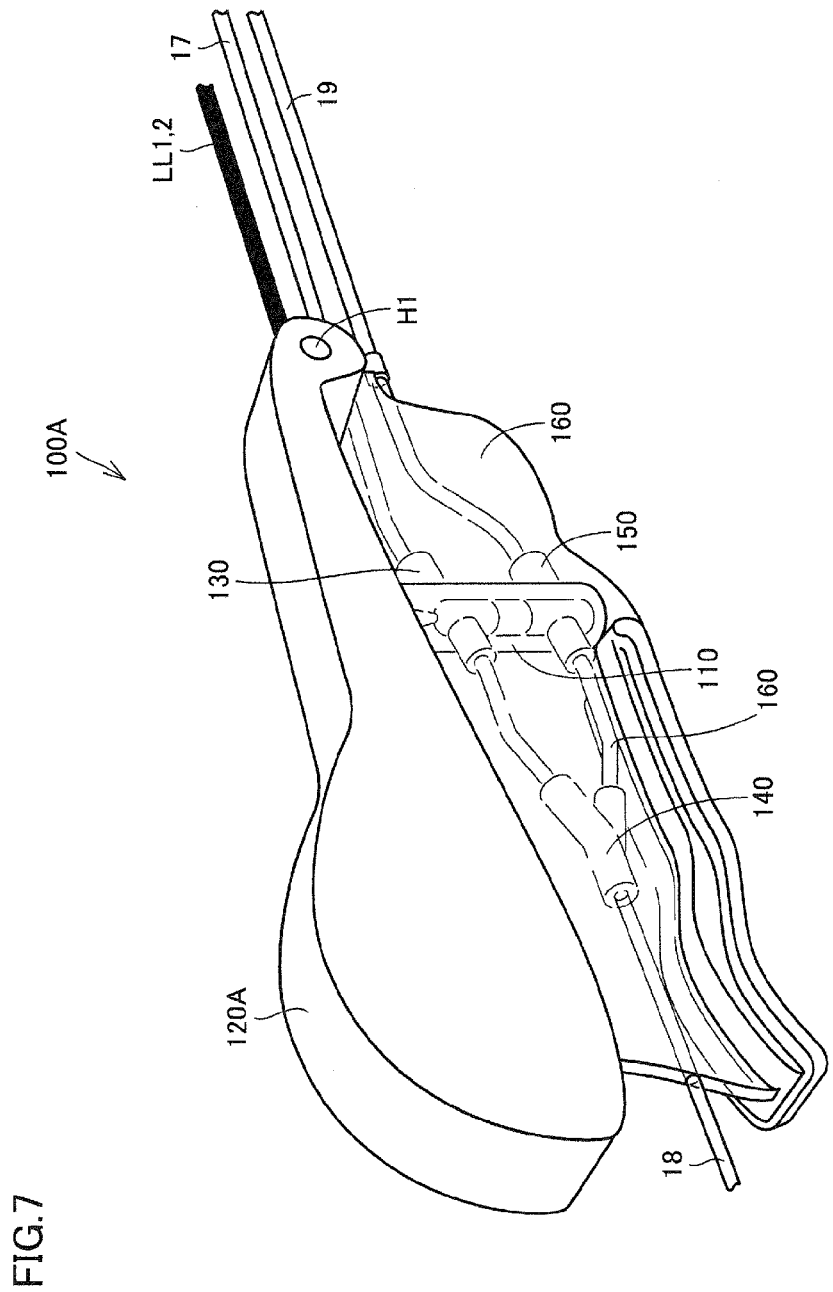
FIG. 7 is a first perspective view showing a specific usage pattern of the valve-equipped hand switch in the embodiment.
Figure 8:
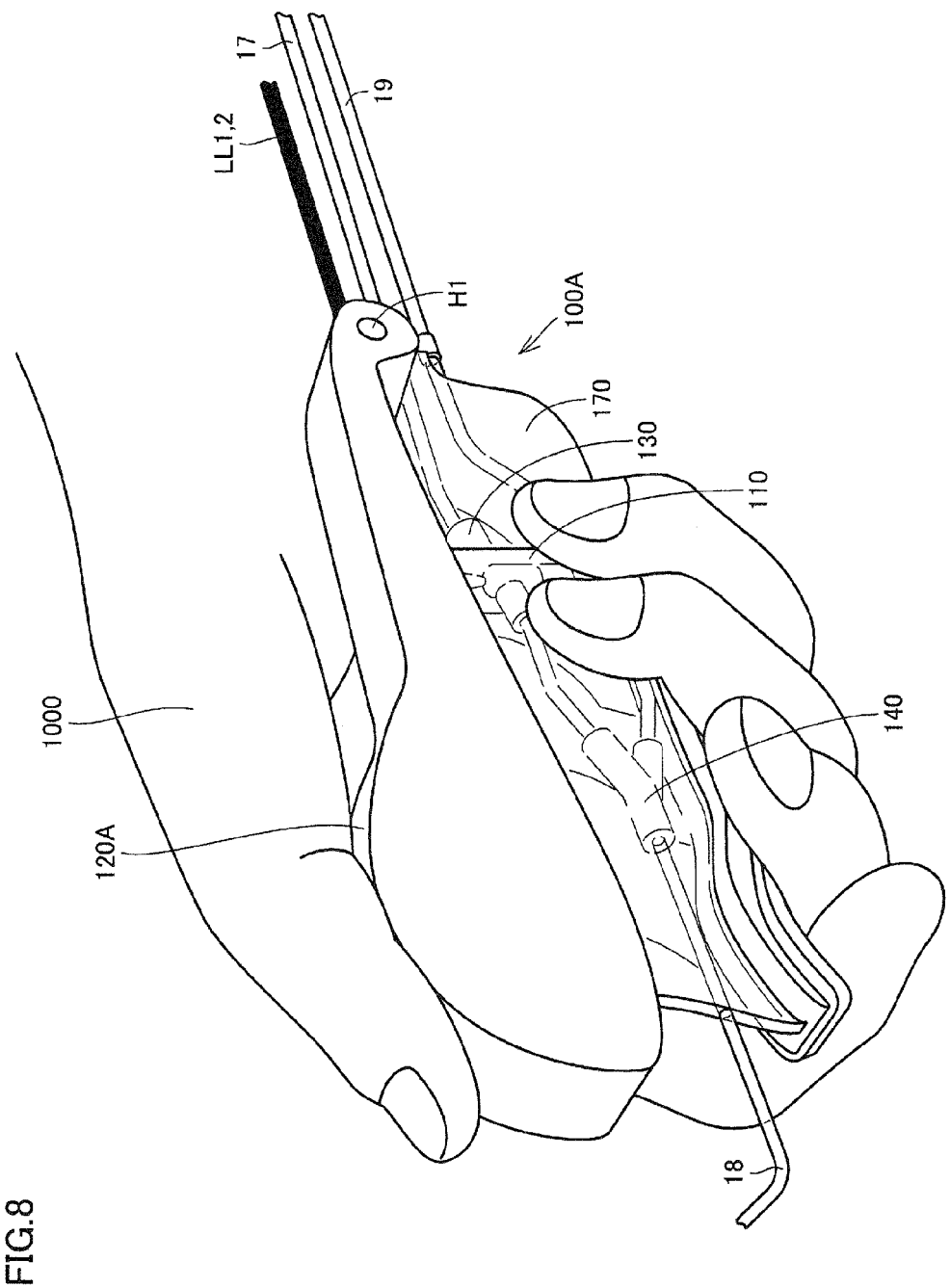
FIG. 8 is a second perspective view showing the specific usage pattern of the valve-equipped hand switch in the embodiment.

Valve-equipped hand switch 100A shown in FIGS. 7 and 8 includes detection device 50 above valve 110. Alternatively, as shown in FIGS. 9 and 10, detection device 50 may be separated from valve 110 and provided on the side of a tip end of lever 120A (opposite to hinge H1) so that detection device 50 operates in conjunction with movement of operation piston 120.

Figure 9:
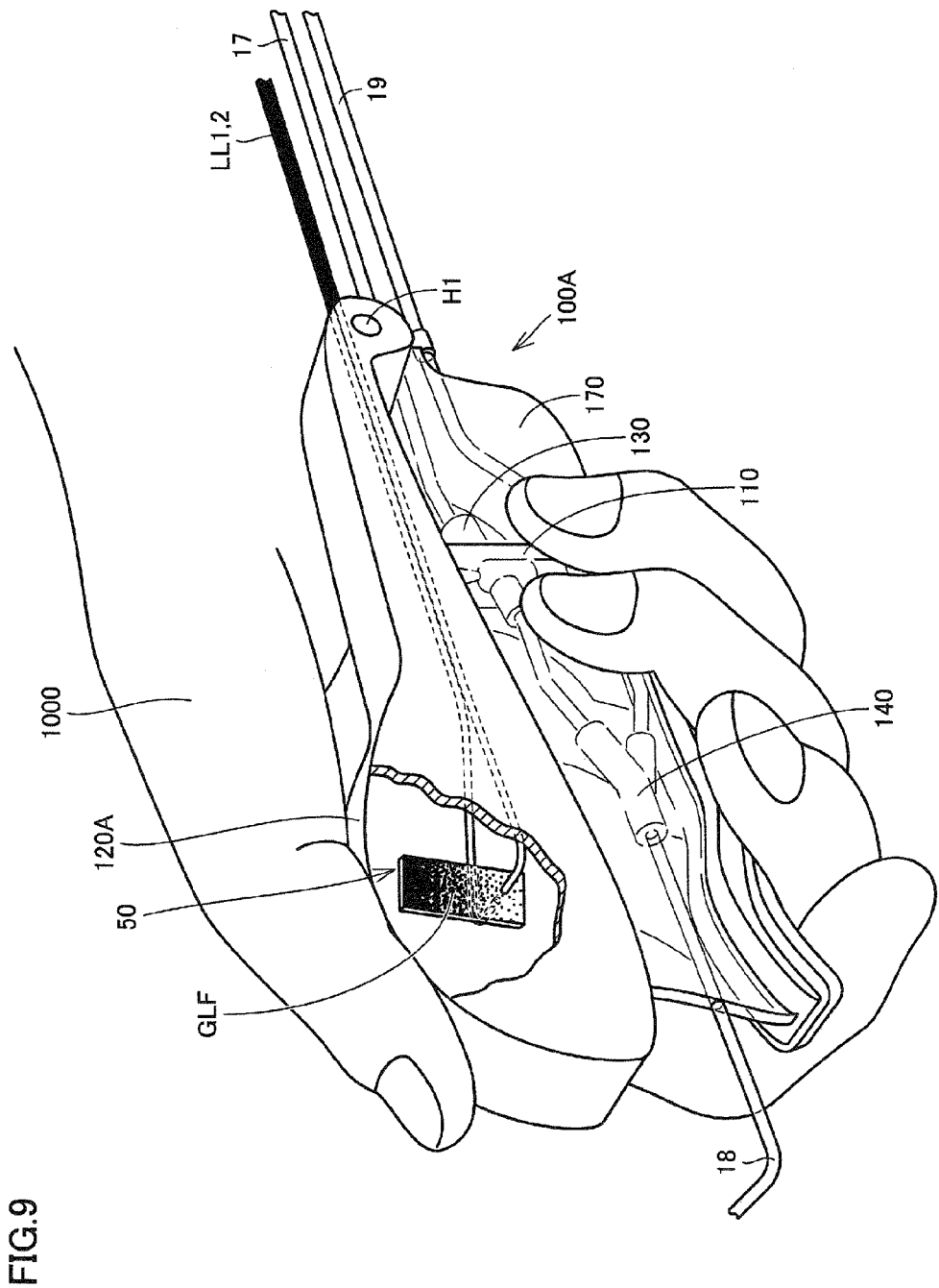
FIG. 9 is a first perspective view showing another specific usage pattern of the valve-equipped hand switch in the embodiment.
Figure 10:
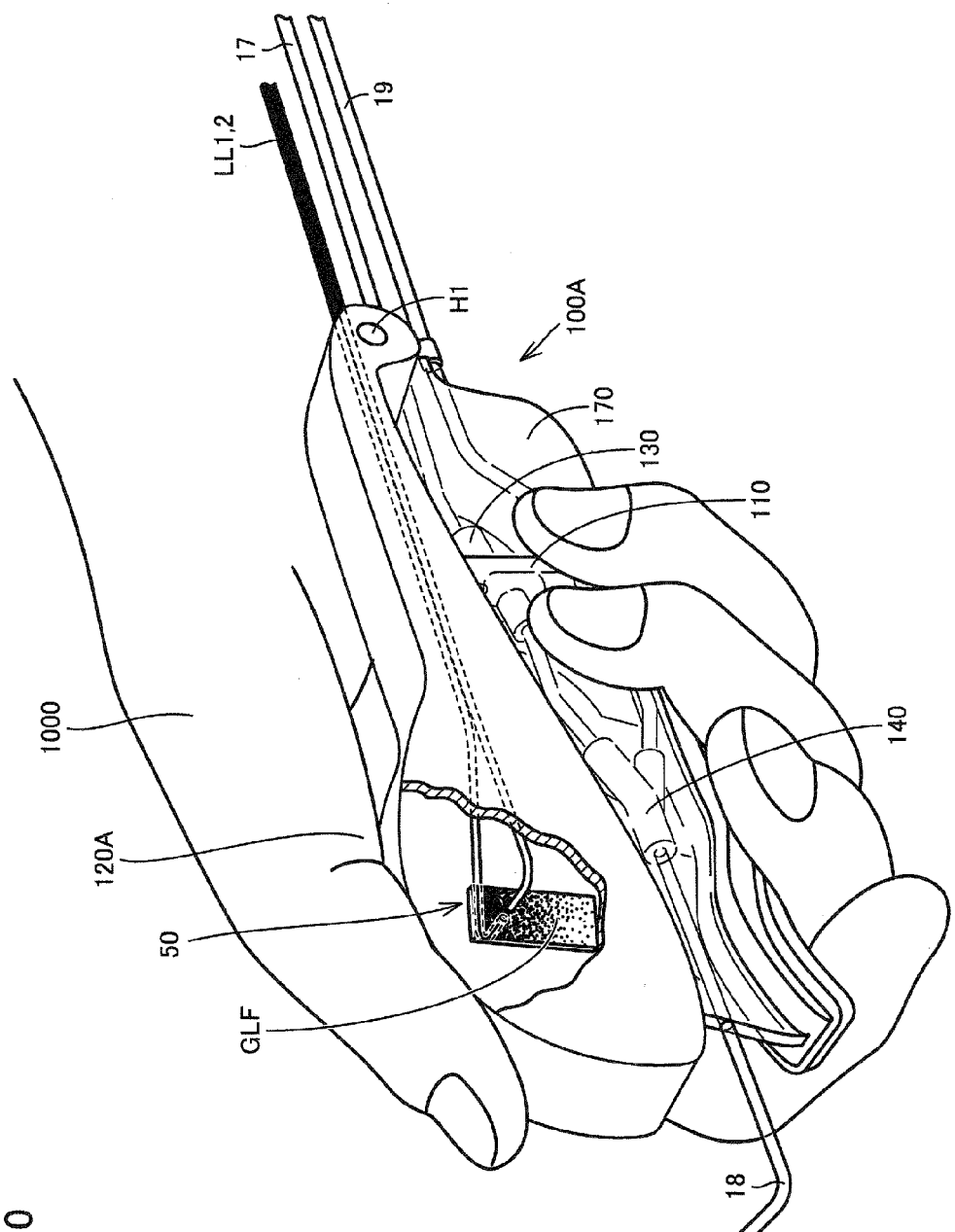
FIG. 10 is a second perspective view showing the another specific usage pattern of the valve-equipped hand switch in the embodiment.

Relative to the position of lever 120A in FIG. 9, FIG. 10 shows a state where lever 120A has been pushed completely. As a result, a stroke of gradation light transmission portion GLF can be increased, thereby improving accuracy in detecting a rate of movement and an amount of movement of gradation light transmission portion GLF.

(Double Syringe Type Chemical Liquid Introduction Device 500A)

Figure 11:
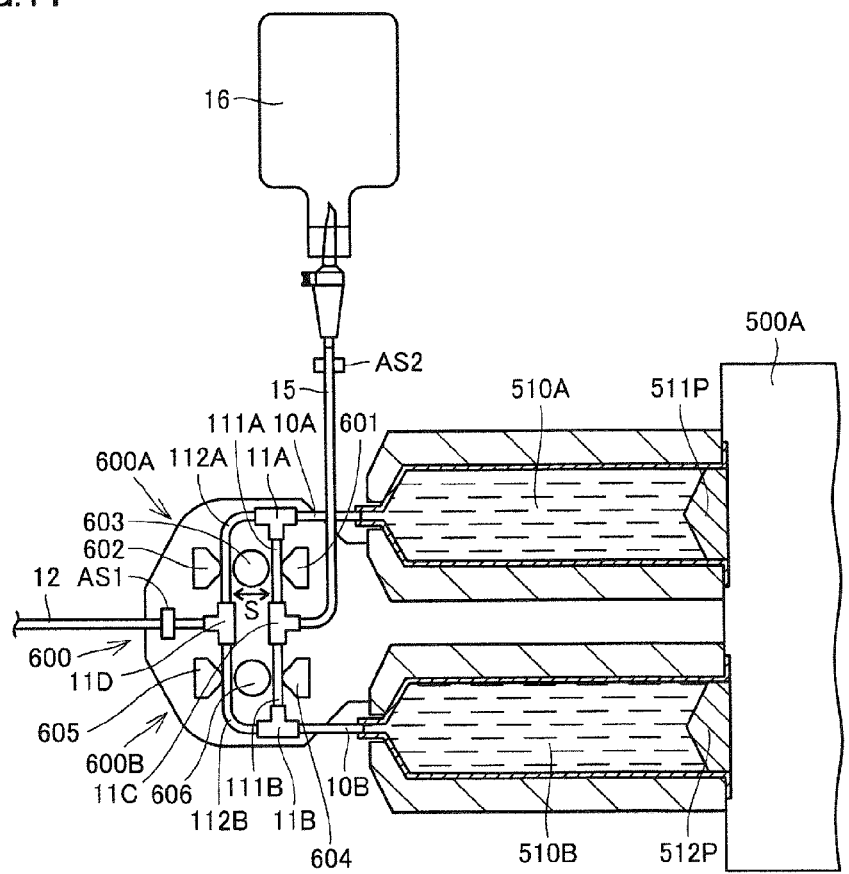
FIG. 11 shows a flow path structure when a double syringe is used in the chemical liquid introduction system in the embodiment.
Figure 12:
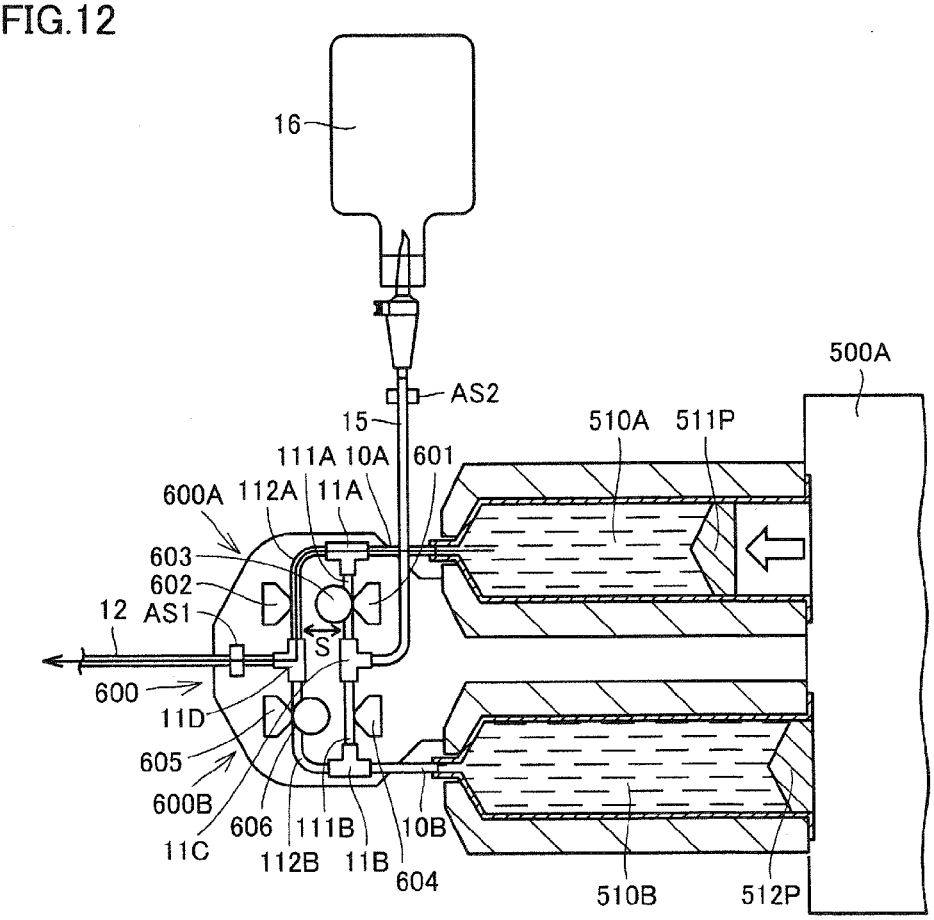
FIG. 12 is a first schematic diagram showing a step of suctioning and introducing a contrast medium when the double syringe is used in the chemical liquid introduction system in the embodiment.
Figure 13:
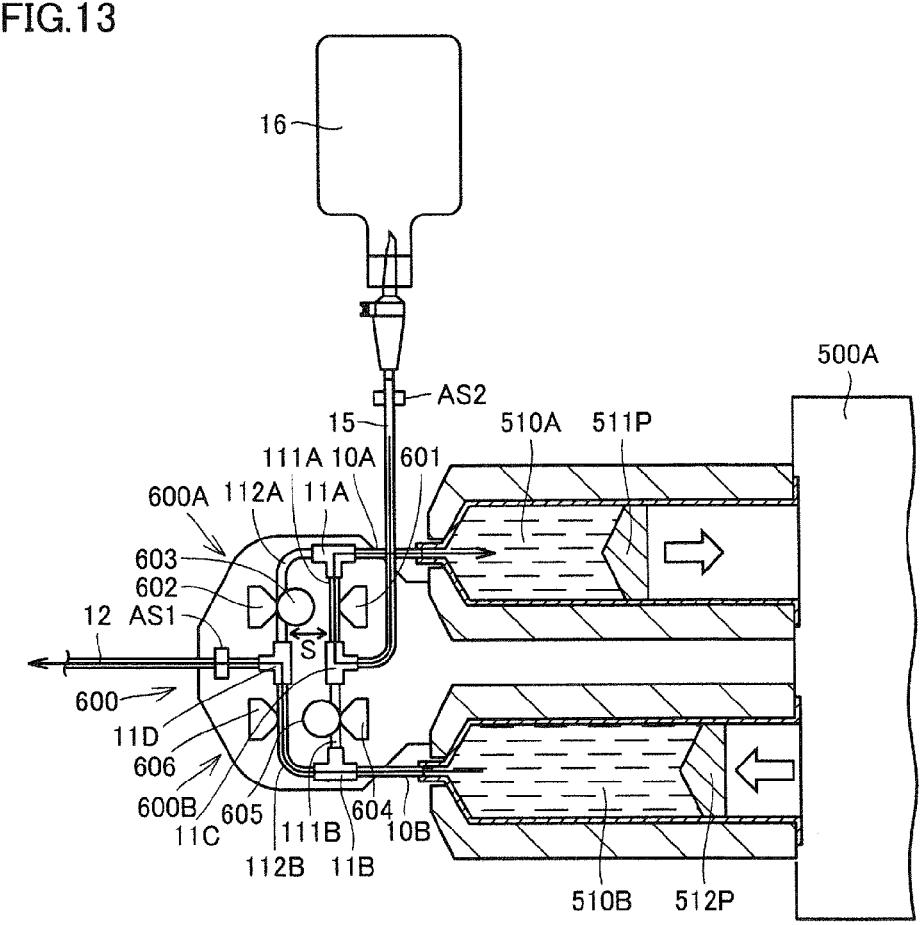
FIG. 13 is a second schematic diagram showing the step of suctioning and introducing the contrast medium when the double syringe is used in the chemical liquid introduction system in the embodiment.
Figure 14:
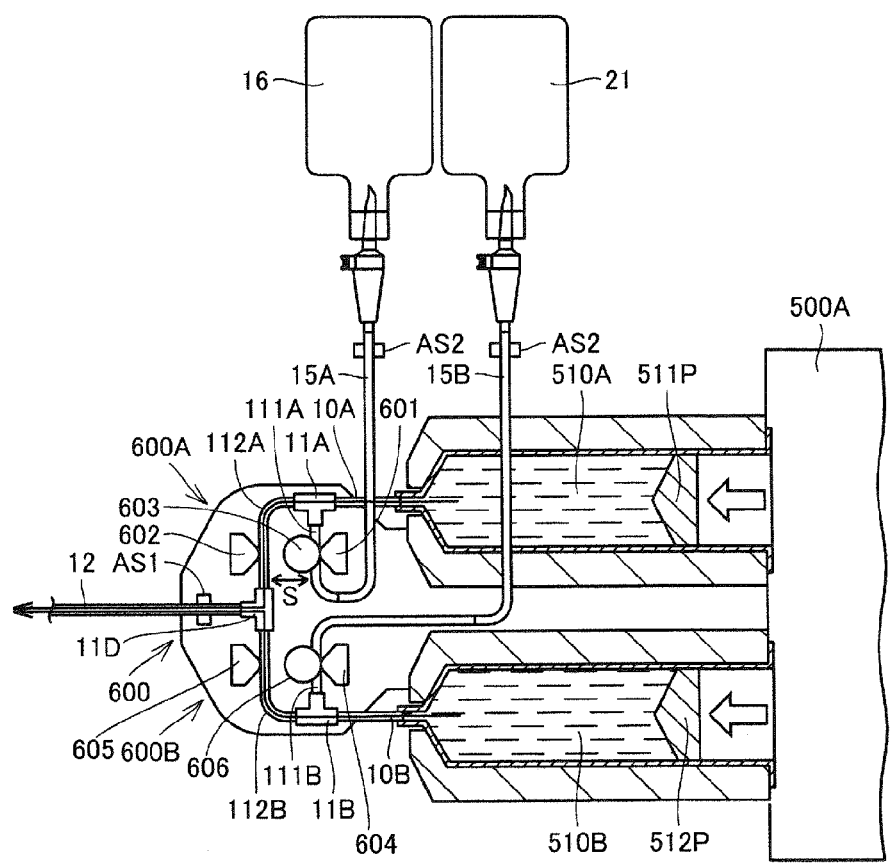
FIG. 14 is a schematic diagram showing mixing introduction of a contrast medium and physiological saline when the double syringe is used in the chemical liquid introduction system in the embodiment.

Referring now to FIGS. 11 to 14, a case where a double syringe type chemical liquid introduction device 500A is used in the chemical liquid introduction system in this embodiment is described. Valve-equipped hand switch 100 has the same structure, and a step of suctioning and introducing a contrast medium is described below. FIG. 11 shows a flow path structure when a double syringe is used, FIGS. 12 and 13 are first and second schematic diagrams showing a step of suctioning and introducing a contrast medium when the double syringe is used, and FIG. 14 is a schematic diagram showing mixing introduction of a contrast medium and physiological saline.

Referring to FIG. 11, chemical liquid introduction device 500A is attached to a first syringe 510A filled with a contrast medium, and a second syringe 510B filled with a contrast medium. First syringe 510A includes a first plunger 511P therein, and second syringe 510B includes a second plunger 512P therein.

First syringe 510A is coupled to one end of a first flow path 10A. First flow path 10A has the other end coupled to a first three-way cock 11A. First three-way cock 11A is coupled to one end of each of a second flow path 111A and a third flow path 112A.

Second syringe 510B is coupled to one end of a fourth flow path 10B. Fourth flow path 10B has the other end coupled to a second three-way cock 11B. Second three-way cock 11B is coupled to one end of each of a fifth flow path 111B and a sixth flow path 112B.

Second flow path 111A and fifth flow path 111B each has the other end coupled to a third three-way cock 11C. Third three-way cock 11C is coupled to flow path 15 having the other end coupled to contrast medium bag 16.

Third flow path 112A and sixth flow path 112B each has the other end coupled to a fourth three-way cock 11D. Fourth three-way cock 11D is coupled to flow path 12 having the other end coupled to coupling connector 13.

Flow path 12 is provided with an air sensor AS1 for sensing air mixed into the flow path, and flow path 15 is provided with an air sensor AS2 for sensing air mixed into the flow path.

(Flow Path Switching Device 600)

A flow path switching device 600 for switching between opening and closing of second flow path 111A and between opening and closing of third flow path 112A is further provided. Flow path switching device 600 includes a first flow path switching device 600A and a second flow path switching device 600B.

First flow path switching device 600A is provided to switch between second flow path 111A and third flow path 112A arranged parallel to each other. Second flow path switching device 600B is provided to switch between fifth flow path 111B and sixth flow path 112B arranged parallel to each other.

First flow path switching device 600A includes a first switching valving element 603 arranged between second flow path 111A and third flow path 112A in a manner movable in a direction (direction of S in FIG. 11) intersecting a direction in which the flow paths extend. First flow path switching device 600A also includes a first fixed valving element 601 and a second fixed valving element 602 in positions opposite to first switching valving element 603 across the flow paths, respectively.

Likewise, second flow path switching device 600B includes a second switching valving element 606 arranged between fifth flow path 111B and sixth flow path 112B in a manner movable in a direction (direction of S in FIG. 11) intersecting a direction in which the flow paths extend. Second flow path switching device 600B also includes a third fixed valving element 604 and a fourth fixed valving element 605 in positions opposite to second switching valving element 606 across the flow paths, respectively.

Referring now to FIGS. 12 and 13, a step of suctioning and introducing a contrast medium using flow path switching device 600 having the above structure is described. First, as shown in FIG. 12, first switching valving element 603 of first flow path switching device 600A is moved toward first fixed valving element 601, to close second flow path 111A. In addition, second switching valving element 606 of second flow path switching device 600B is moved toward fourth fixed valving element 605, to close sixth flow path 112B.

Consequently, first syringe 510A becomes in communication with flow path 12. By driving chemical liquid introduction device 500A, first plunger 511P moves forward to deliver the contrast medium inside to patient line 18 through valve-equipped hand switch 100.

Referring now to FIG. 13, when the contrast medium in first syringe 510A becomes empty, flow path switching device 600 switches between first flow path switching device 600A and second flow path switching device 600B. Specifically, first switching valving element 603 of first flow path switching device 600A is moved toward second fixed valving element 602, to close third flow path 112A. In addition, second switching valving element 606 of second flow path switching device 600B is moved toward third fixed valving element 604, to close fifth flow path 111B.

Consequently, first syringe 510A becomes in communication with contrast medium bag 16, and second syringe 510B becomes in communication with flow path 12. By simultaneously performing operation of moving first plunger 511P of first syringe 510A backward and operation of moving second plunger 512P of second syringe 510B forward in this state, a step of suctioning the contrast medium into first syringe 510A and a step of introducing the contrast medium from second syringe 510B can be simultaneously performed. If it is not necessary to perform the step of suctioning the contrast medium into first syringe 510A, first plunger 511P does not need to be moved backward.

Likewise, by simultaneously performing operation of moving first plunger 511P of first syringe 510A forward and operation of moving second plunger 512P of second syringe 510B backward, a step of introducing the contrast medium from first syringe 510A and a step of suctioning the contrast medium into second syringe 510B can be simultaneously performed.

(Mixing Introduction)

As shown in FIG. 14, by coupling second flow path 111A directly to a flow path 15A coupled to contrast medium bag 16, and coupling fifth flow path 111B directly to a flow path 15B coupled to physiological saline bag 21, without using third three-way cock 11C, mixing introduction can be implemented.

Specifically, first switching valving element 603 of first flow path switching device 600A is moved toward first fixed valving element 601, to close second flow path 111A. In addition, second switching valving element 606 of second flow path switching device 600B is moved toward third fixed valving element 604, to close fifth flow path 111B. Consequently, first syringe 510A and second syringe 510B become in communication with flow path 12, allowing mixing introduction of the contrast medium and the physiological saline into patient line 18.

By switching between first switching valving element 603 of first flow path switching device 600A and second switching valving element 606 of second flow path switching device 600B to close third flow path 112A and fifth flow path 111B, suctioning of the contrast medium into first syringe 510A and suctioning of the physiological saline into second syringe 510B can be simultaneously performed.

Although the embodiments of the present invention have been described above, it should be understood that the embodiments disclosed herein are illustrative and non-restrictive in every respect. The scope of the present invention is defined by the terms of the claims, and is intended to include any modifications within the scope and meaning equivalent to the terms of the claims.

REFERENCE SIGNS LIST

1 contrast medium introduction system; 10 flow path; 10A first flow path; 10B fourth flow path; 11D fourth three-way cock; 12, 15, 15A, 15B, 20 flow path; 11 branch tube; 11A first three-way cock; 11B second three-way cock; 11C third three-way cock; 12, 15 flow path; 13, 14 coupling connector; 16 contrast medium bag; 21 physiological saline bag; 17 chemical liquid line; 18 patient line; 19 blood pressure monitor line; 50 detection device; 100 valve-equipped hand switch; 100A valve-equipped hand switch; 110 valve; 110 valve; 110a one end side; 110b other end side; 111 main passage; 111A second flow path; 111B fifth flow path; 112A third flow path; 112B sixth flow path; 120 operation piston; 120A lever; 121 first plunger; 122 handle portion; 123 second plunger; 123a main plunger; 123b auxiliary plunger; 124 cap; 125 elastic member; 126 spacer shaft; 127 third plunger; 128 spacer portion; 130 first branch tube; 131 first port; 141 second port; 151 third port; 140 second branch tube; 141 second port; 150 third branch tube; 151 third port; 160 coupling tube; 161 fourth port; 170 grip body; 200 flow path opening/closing device; 210 movable object; 300 blood pressure measurement device (BPT); 310 monitor; 400 roller pump; 500, 500A chemical liquid introduction device; 510 syringe; 510A first syringe; 510B second syringe; 510B second syringe; 511P first plunger; 512P second plunger; 600 flow path switching device; 600A first flow path switching device; 600B second flow path switching device; 601 first fixed valving element; 602 second fixed valving element; 603 first switching valving element; 604 third fixed valving element; 605 fourth fixed valving element; 606 second switching valving element; 700 patient; 760 catheter; 1000 operator; AS1, AS2 air sensor; GLF gradation light transmission portion; H1 hinge; LL1 laser light application line; LL2 laser light reception line.

The invention claimed is:

1. A valve-equipped hand switch comprising:
    a valve having a main passage with one open end side and other closed end side;
    a first port in communication with a side portion of a central area of said main passage;
    a second port in communication with a side portion of said main passage closer to the other end side than said first port of the central area;
    a third port in communication with the side portion of said main passage closer to the other end side than said second port;
    a fourth port in communication with the side portion of said main passage closer to the other end side than said second port, and also in communication with said second port;
    a first plunger fixedly arranged on the other end side in said main passage, for controlling a communicated state and a cutoff state between said third port and said fourth port;
    a second plunger slidably arranged in a liquid-tight manner in said main passage to divide said main passage into two segments, said one end side and said other end side, and also arranged with an elastic member interposed between itself and said first plunger;
    a third plunger slidably arranged in a liquid-tight manner in said main passage, on a tip end portion of an operation piston inserted into said main passage through said one end side;
    a spacer portion having a diameter smaller than an inner diameter of said main passage, and fixed to a side of said third plunger closer to said second plunger; and
    a detection device provided to operate in conjunction with movement of said operation piston, for detecting a rate of insertion and an amount of insertion movement of said operation piston in said main passage, wherein
    in an initial state,
    a communicated state between said third port and said fourth port is selected with said first plunger, and
    a cutoff state between said first port and said second port is selected with said second plunger, and
    in an operation state,
    a communicated state between said first port and said second port is selected by pushing said operation piston toward said other end side of said main passage, causing said spacer portion to oppose an elastic force resulting from compression of said elastic member while abutting said second plunger, to move said second plunger toward said other end side of said main passage, leading said spacer portion to be positioned between said first port and said second port, and
    a cutoff state between said third port and said fourth port is selected with said first plunger due to said first plunger being pushed by said elastic member.

2. The valve-equipped hand switch according to claim 1, wherein
    said first plunger includes an elastic member, and
    a circumferential surface of said first plunger bulges outward by being pushed by said elastic member, to attain a cutoff state between said third port and said fourth port.

3. The valve-equipped hand switch according to claim 1, wherein
    in a state where a pressure equal to or higher than a prescribed pressure is applied from said first port,
    said second plunger is biased toward said other end side of said main passage by the pressure, to attain a cutoff state between said third port and said fourth port, and
    said third plunger and said spacer portion are biased toward said one end side of said main passage, to attain a communicated state between said first port and said second port.

4. The valve-equipped hand switch according to claim 1, wherein
    said first port is coupled to a chemical liquid line, said second port is coupled to a patient line, and
said third port is coupled to a blood pressure monitor line.

5. The valve-equipped hand switch according to claim 4, wherein
said chemical liquid line is coupled to an injector.

6. A chemical liquid introduction system comprising:
a chemical liquid line coupled to an injector;
a patient line;
a blood pressure monitor line; and
a valve-equipped hand switch including a first port coupled to said chemical liquid line, a second port coupled to said patient line, and a third port coupled to said blood pressure monitor line, wherein
said valve-equipped hand switch includes a valve having a main passage with one open end side and other closed end side,
said first port is in communication with a side portion of a central area of said main passage,
said second port is in communication with a side portion of said main passage closer to the other end side than said first port of the central area,
said third port is in communication with a side portion of said main passage closer to the other end side than said second port,
a fourth port is in communication with the side portion of said main passage closer to the other end side than said second port, and also in communication with said second port,
said main passage includes therein
a first plunger fixedly arranged on the other end side in said main passage, for controlling a communicated state and a cutoff state between said third port and said fourth port,
a second plunger slidably arranged in a liquid-tight manner in said main passage to divide said main passage into two segments, said one end side and said other end side, and also arranged with an elastic member interposed between itself and said first plunger,
a third plunger slidably arranged in a liquid-tight manner in said main passage, on a tip end portion of an operation piston inserted into said main passage through said one end side,
a spacer portion having a diameter smaller than an inner diameter of said main passage, and fixed to a side of said third plunger closer to said second plunger, and
a detection device provided to operate in conjunction with movement of said operation piston, for detecting a rate of insertion and an amount of insertion movement of said operation piston in said main passage,
in an initial state,
a communicated state between said third port and said fourth port is selected with said first plunger, and
a cutoff state between said first port and said second port is selected with said second plunger,
in an operation state,
a communicated state between said first port and said second port is selected by pushing said operation piston toward said other end side of said main passage, causing said spacer portion to oppose an elastic force resulting from compression of said elastic member while abutting said second plunger, to move said second plunger toward said other end side of said main passage, leading said spacer portion to be positioned between said first port and said second port, and
a cutoff state between said third port and said fourth port is selected with said first plunger due to said first plunger being pushed by said elastic member, and
in a state where a pressure equal to or higher than a prescribed pressure is applied from said first port coupled to said chemical liquid line,
said second plunger is biased toward said other end side of said main passage by the pressure, to attain a cutoff state between said third port and said fourth port, and
said third plunger and said spacer portion are biased toward said one end side of said main passage, to attain a communicated state between said first port and said second port.

7. The chemical liquid introduction system according to claim 6, wherein
said chemical liquid line includes a segment of a chemical liquid introduction device and a segment of said valve-equipped hand switch that are attachable to/detachable from each other.

* * * * *